United States Patent
Millett et al.

(10) Patent No.: US 10,238,302 B2
(45) Date of Patent: *Mar. 26, 2019

(54) PRESSURE-SENSING INTRAVASCULAR DEVICES, SYSTEMS, AND METHODS

(71) Applicant: Volcano Corporation, San Diego, CA (US)

(72) Inventors: Bret C. Millett, Folsom, CA (US); David H. Burkett, Temecula, CA (US); Paul Douglas Corl, Palo Alto, CA (US)

(73) Assignee: VOLCANO CORPORATION, San Diego, CA (US)

( * ) Notice: Subject to any disclaimer, the term of this patent is extended or adjusted under 35 U.S.C. 154(b) by 750 days.

This patent is subject to a terminal disclaimer.

(21) Appl. No.: 14/133,374

(22) Filed: Dec. 18, 2013

(65) Prior Publication Data

US 2014/0180143 A1  Jun. 26, 2014

Related U.S. Application Data

(60) Provisional application No. 61/745,014, filed on Dec. 21, 2012, provisional application No. 61/745,493, (Continued)

(51) Int. Cl.
*A61B 5/02* (2006.01)
*H01R 43/00* (2006.01)
(Continued)

(52) U.S. Cl.
CPC .......... *A61B 5/0215* (2013.01); *A61B 5/6851* (2013.01); *A61B 5/0066* (2013.01);
(Continued)

(58) Field of Classification Search
CPC combination set(s) only.
See application file for complete search history.

(56) References Cited

U.S. PATENT DOCUMENTS

2003/0216621 A1 11/2003 Alpert
2005/0091833 A1* 5/2005 Kiepen ............... A61B 5/0215
29/594
(Continued)

FOREIGN PATENT DOCUMENTS

JP    2006204378 A    8/2006
WO   WO 2012-109039 A1   8/2012

OTHER PUBLICATIONS

International Search Report and Written Opinion received in Patent Cooperation Treaty Application No. PCT/US2013/075370, dated Apr. 8, 2014, 15 pages.

*Primary Examiner* — Christian Jang
*Assistant Examiner* — Mitchell E Alter

(57) ABSTRACT

Intravascular devices, systems, and methods are disclosed. In some embodiments, the intravascular devices include at least one pressure sensing component within a distal portion of the device. In that regard, one or more electrical, electronic, optical, and/or electro-optical pressure-sensing components is secured to an elongated substrate such that the pressure-sensing component is mounted perpendicular to a central longitudinal axis of the device. In some implementations, the elongated substrate has a cylindrical profile. Methods of making, assembling, and/or using such intravascular devices and associated systems are also provided.

23 Claims, 8 Drawing Sheets

Related U.S. Application Data filed on Dec. 21, 2012, provisional application No. 61/785,390, filed on Mar. 14, 2013.

(51) Int. Cl.
*A61B 8/00* (2006.01)
*A61B 5/0215* (2006.01)
*A61B 5/00* (2006.01)
*A61B 8/12* (2006.01)

(52) U.S. Cl.
CPC .............. *A61B 5/0084* (2013.01); *A61B 8/12* (2013.01); *A61B 8/445* (2013.01); *Y10T 29/49117* (2015.01)

(56) References Cited

U.S. PATENT DOCUMENTS

| | | | |
|---|---|---|---|
| 2009/0088650 A1* | 4/2009 | Corl | A61B 5/0215 600/486 |
| 2009/0118643 A1 | 5/2009 | Smith et al. | |
| 2010/0312115 A1* | 12/2010 | Dentinger | A61B 5/02116 600/450 |
| 2011/0034912 A1* | 2/2011 | de Graff | H01L 27/14618 606/21 |
| 2011/0072659 A1 | 3/2011 | Swanson et al. | |
| 2011/0201906 A1 | 8/2011 | Samuelsson | |
| 2011/0245693 A1* | 10/2011 | Hastings | A61B 5/0215 600/486 |
| 2013/0324863 A1* | 12/2013 | Yu | A61M 25/09 600/486 |
| 2014/0180142 A1 | 6/2014 | Millett et al. | |

* cited by examiner

PRESSURE-SENSING INTRAVASCULAR DEVICES, SYSTEMS, AND METHODS

CROSS-REFERENCE TO RELATED APPLICATIONS

The present application claims priority to and the benefit of U.S. Provisional Patent Application No. 61/745,014, filed Dec. 21, 2012, U.S. Provisional Patent Application No. 61/745,493, filed Dec. 21, 2012, and U.S. Provisional Patent Application No. 61/785,390, filed Mar. 14, 2013, each of which is hereby incorporated by reference in its entirety.

TECHNICAL FIELD

The present disclosure relates generally to intravascular devices, systems, and methods. In some embodiments, the intravascular devices are guide wires that include one or more electrical, electronic, optical, or electro-optical sensors positioned at a distal end.

BACKGROUND

Heart disease is a critical healthcare issue for the individual patient and for society as a whole. Recent research has shown that treatment of heart disease, when guided by improved diagnostic methods such as functional assessment of the coronary circulation using intravascular pressure measurements, leads to both improved quality of life for the patient and reduced healthcare costs for society.

Intravascular catheters and guide wires are commonly utilized to measure the pressure within the blood vessel, to visualize the inner lumen of the blood vessel, and/or to otherwise obtain diagnostic information related to the blood vessel. To date, guide wires containing pressure sensors, imaging elements, and/or other electrical, electronic, optical, or electro-optical components have suffered from poor mechanical performance in comparison to standard guide wires that do not include such components. Existing pressure-sensing guide wires typically incorporate a single pressure sensor located approximately 3 cm from the distal tip of the guide wire. Since the sensor is fixed in position on the guide wire, the pressure can only be measured at different locations within the vasculature by advancing or retracting the entire guide wire to position the sensor at the desired location. Traditionally, the pressure-sensing guide wire includes a sensor formed on a planar substrate and having terminals attached to the conductors of a cable which runs through the intravascular device. The sensor substrate is typically oriented such that the pressure sensitive portion faces radially outward into the blood stream. It is generally desired to separate the substrate slightly away from the walls of the intravascular device in order to mechanically isolate the pressure sensor substrate from the guide wire structure, so that bending and torsional stresses are not coupled to the sensor substrate where they could adversely affect the pressure measurement accuracy. This pressure sensing guide wire geometry provides access for intravascular pressure measurement, but results in compromises to the mechanical structure which lead to poor mechanical performance compared to that of a conventional guide wire without measurement capability. Furthermore, the fragile electrical interconnects between the sensor terminals and the electrical leads are vulnerable to failure. In this conventional configuration the small diameter of the intravascular device introduces places constraints on the sensor dimensions, exacerbating the limitations and associated problems.

Accordingly, there remains a need for improved intravascular devices, systems, and methods that preserve the desirable mechanical properties of the device while providing a more robust interconnect to one or more electrical, electronic, optical, or electro-optical components.

SUMMARY

According to embodiments disclosed herein an intravascular sensor assembly may include a flexible elongate member having a longitudinal axis (LA); a core member disposed inside the flexible elongate member; and an elongated substrate disposed distal to the core member and inside the flexible elongate member, the elongated substrate including at least one electrode disposed within at least one recess in an outer surface of the elongated substrate, the at least one recess extending in a longitudinal direction; and a sensor circuit disposed on a distal surface of the elongated substrate, the sensor circuit coupled to the at least one electrode.

In some instances, a pressure-sensing guide wire is provided. The pressure-sensing guide wire includes a pressure sensor mounted such that a membrane of the pressure sensor extends across a width of the guide wire, instead of along the length of the guide wire. As a result of mounting the pressure sensor in this orientation, the thickness, robustness, and durability of the pressure sensor can be increased while staying within the limited space provided by the outer profile of the guide wire.

According to embodiments disclosed herein a sensor structure for use in an intravascular device assembly may include a substrate having an elongated shape with a length defined along a longitudinal axis (LA) and a width extending perpendicular to the longitudinal axis, the shape further including a proximal surface and an opposing distal surface, each extending substantially perpendicular to the LA; and an outer surface extending substantially parallel to the LA between the proximal and distal surfaces; at least one electrode disposed longitudinally within at least one recess in the outer surface of the substrate, and a sensor circuit disposed on the distal surface, the sensor circuit having at least one lead or conductor coupled to the at least one electrode.

A system for performing measurements using a sensor exposed to an intravascular environment, the system including an intravascular device having: a flexible elongate member having a longitudinal axis (LA); a core member disposed inside the flexible elongate member; and an elongated substrate disposed distal to the core member and inside the flexible elongate member, the elongated substrate including at least one electrode disposed within at least one recess in an outer surface of the elongated substrate, the at least one recess extending in a longitudinal direction; and a sensor circuit disposed on a distal surface of the elongated substrate, the sensor circuit coupled to the at least one electrode; and a control console coupled to the intravascular device.

According to embodiments disclosed herein a method of forming a pressure-sensing guide wire may include forming an elongated substrate; forming a plurality of recesses in an outer surface of the elongated substrate; filling at least a portion of each of the recesses with a conductive material to form a plurality of electrodes; fabricating a sensor circuit on a front surface of the elongated substrate, the front surface extending perpendicular to a longitudinal axis of the elongated substrate; electrically coupling the plurality of electrode to terminals of the sensor circuit; electrically coupling a plurality of conductors of a communication cable to the plurality of electrodes; and securing the elongated substrate to a distal portion of a flexible elongate member.

These and other embodiments of the present invention will be described in further detail below with reference to the following drawings.

BRIEF DESCRIPTION OF THE DRAWINGS

In the figures, elements having the same reference number have the same or similar functions.

DETAILED DESCRIPTION

Figure 1:
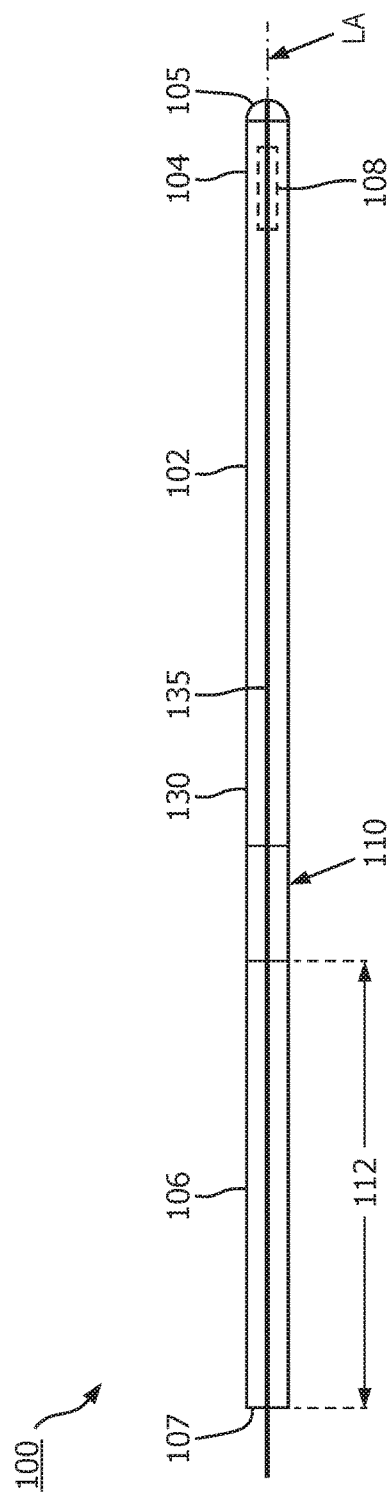
FIG. 1 is a diagrammatic, schematic side view of an intravascular device according to some embodiments.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While each of the illustrated embodiments of the present disclosure includes a flexible elongate member having a cylindrical form with a circular cross-sectional profile that defines an outer diameter of the flexible elongate member, in other instances all or a portion of the flexible elongate member may have other geometric cross-sectional profiles (e.g., oval, rectangular, square, elliptical, etc.) or non-geometric cross-sectional profiles. Flexible elongate members include, for example, guide wires and catheters. In that regard, a catheter may or may not include a lumen extending along its length for receiving and/or guiding other instruments. If the catheter includes a lumen, the lumen may be centered or offset with respect to the cross-sectional profile of the device.

In most embodiments of the present disclosure, the flexible elongate member includes one or more electrical, electronic, optical, or electro-optical components. For example, without limitation, a flexible elongate member may include one or more of the following types of components: a pressure sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data from or deliver therapy to a vessel or other portion of the anatomy in which the flexible elongate member is disposed. Often the components are also configured to communicate with an external device for processing, display, activation, and/or control. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electrical, electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electrical or electronic components. Such housing portions can be tubular structures attached to the distal portion of the elongate member. Some flexible elongate members are tubular and have one or more lumens in which the electrical or electronic components can be positioned within the distal portion. In some embodiments, the distal portion does not include a separate housing for mounting the electrical, electronic, optical, and/or electro-optical component(s). In such instances, the distal portion may have an outer diameter equal to the outer diameter of the flexible elongate member. In some instances, the distal portion is coupled to proximal and distal flexible elements (e.g., coils, flexible tubing, etc.). Accordingly, in some implementations the distal portion includes a step-down outer diameter at each end such that the reduced outer diameter is slightly smaller than the inner diameter of the proximal and distal flexible elements. In other implementations, the distal portion has a uniform outer diameter that is slightly smaller than the inner diameter of the distal and proximal flexible elements.

The electrical, electronic, optical, and/or electro-optical components and the associated communication lines are sized and shaped to allow for the diameter of the flexible elongate member to be very small. For example, the outside diameter of the elongate member, such as a guide wire or catheter, containing one or more electrical, electronic, optical, and/or electro-optical components as described herein are between about 0.007" (0.178 mm) and about 0.118" (3.0 mm), with some particular embodiments having outer diameters of approximately 0.014" (0.356 mm) and approximately 0.018" (0.457 mm). In some embodiments, the outside diameter of the elongate member may have an OD of 0.035" (0.89 mm). As such, the flexible elongate members incorporating the electrical, electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an member is directly secured to another element, such as being glued or otherwise fastened directly to, on, within, etc. another element, as well as indirect techniques of securing two elements together where one or more elements are disposed between the secured elements.

Sensors used in embodiments consistent with the present disclosure may be positioned within an intravascular device facing an axial direction. In that regard, some embodiments disclosed herein may generally resemble embodiments disclosed in detail in U.S. patent application Ser. No. 11/864,499 entitled "Intravascular Pressure Devices Incorporating Sensors Manufactured Using Deep Reactive Ion Etching," by Paul Douglas Corl, filed on Sep. 28, 2007, the contents of which are hereby incorporated by reference in their entirety, for all purposes. Furthermore, embodiments consistent with the present disclosure provide a robust mounting structure to a pressure sensing circuit facing an axial direction. Thus relaxing the need for a cantilevered sensor decoupled from external stresses induced by guidewire structures. Embodiments as disclosed herein may include sensor circuits formed on a thick wafer substrate that is then disposed on the robust mounting structure.

Referring now to FIG. 1, shown therein is a portion of an intravascular device 100 according to an embodiment of the present disclosure. In that regard, the intravascular device 100 includes a flexible elongate member 102 having a distal portion 104 adjacent a distal end 105 and a proximal portion 106 adjacent a proximal end 107. A component 108 is positioned within the distal portion 104 of the flexible elongate member 102 proximal of the distal tip 105. Generally, the component 108 is representative of one or more electrical, electronic, optical, or electro-optical components. In that regard, the component 108 is a pressure sensor, a temperature sensor, a flow or velocity sensor, an ASIC, a signal conditioning circuit, an RF communication module, a memory module, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned immediately adjacent to the distal tip 105, and in such case, the distal tip may consist of just a thin coating or may be altogether absent. In some instances, the component 108 is positioned within a housing of the flexible elongate member 102. In that regard, the housing is a separate component secured to the flexible elongate member 102 in some instances. In other instances, the component 108 is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member can be any length, in some embodiments the total length is between about 90 cm and about 400 cm, with some specific embodiments having lengths of 140 cm, 190 cm, or 300 cm. Accordingly, in some instances the connector 110 is positioned at the proximal end 107. In other instances, the connector 110 is spaced from the proximal end 107. For example, in some instances the connector 110 is spaced from the proximal end 107 between about 0 cm and about 140 cm. In some specific embodiments, the connector 110 is spaced from the proximal end by a distance of 0 cm, 30 cm, or 140 cm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. Some specific embodiments of electrical conductors in accordance with the present disclosure are discussed below in the context of FIGS. 5-11. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Further, in some embodiments the connector 110 provides both electrical and optical connections to both electrical conductor(s) and optical communication pathway(s) coupled to the component 108. In that regard, it should again be noted that component 108 is comprised of a plurality of elements in some instances. In some instances, the connector 110 is configured to provide a physical connection to another device, either directly or indirectly. In other instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. Generally, any number of electrical conductors, optical pathways, and/or combinations thereof can extend along the length of the flexible elongate member 102 between the connector 110 and the component 108. In some instances, between one and ten electrical conductors and/or optical pathways extend along the length of the flexible elongate member 102 between the connector 110 and the component 108. For the sake of clarity and simplicity, the embodiments of the present disclosure described below include three electrical conductors. However, it is understood that the total number of communication pathways and/or the number of electrical conductors and/or optical pathways is different in other embodiments. More specifically, the number of communication pathways and the number of electrical conductors and optical pathways extending along the length of the flexible elongate member 102 is determined by the desired functionality of the component 108 and the corresponding elements that define component 108 to provide such functionality.

Embodiments consistent with the present disclosure may provide the ability to extend or retract a sensor to multiple locations along the length of the intravascular device—or to expose a fixed sensor to pressures from axially disparate locations by extending or retracting a "snorkel". For example, in some implementations the sensor may be secured to a central core that is mechanically translatable relative to a surrounding elongate member. In embodiments where the sensor is a pressure sensor, blood pressure along the vessel may be mapped without moving the distal tip position of the intravascular device. The distal tip position may remain fixed with the exterior elongated member 130 while the sensor is pulled back with core member 135. Furthermore, an engagement feature of the sensor structure 108 or other associated component may enable torque and rotation of the tip of the wire, if desired. Such embodiments having a pullback capability may be as disclosed in U.S. Provisional Patent Application No. 61/746,537 entitled "Pressure Guide Wire with Sliding Pressure Sensor," filed Dec. 27, 2012, the contents of which are herein incorporated by reference in their entirety, for all purposes. Further, some embodiments include features of the devices disclosed in U.S. Provisional Patent Application No. 61/747,958 entitled "Intravascular Devices Having Artificial Muscles and Associated Systems, and Methods," filed Dec. 31, 2012, the contents of which are herein incorporated by reference in their entirety, for all purposes.

Figure 2:
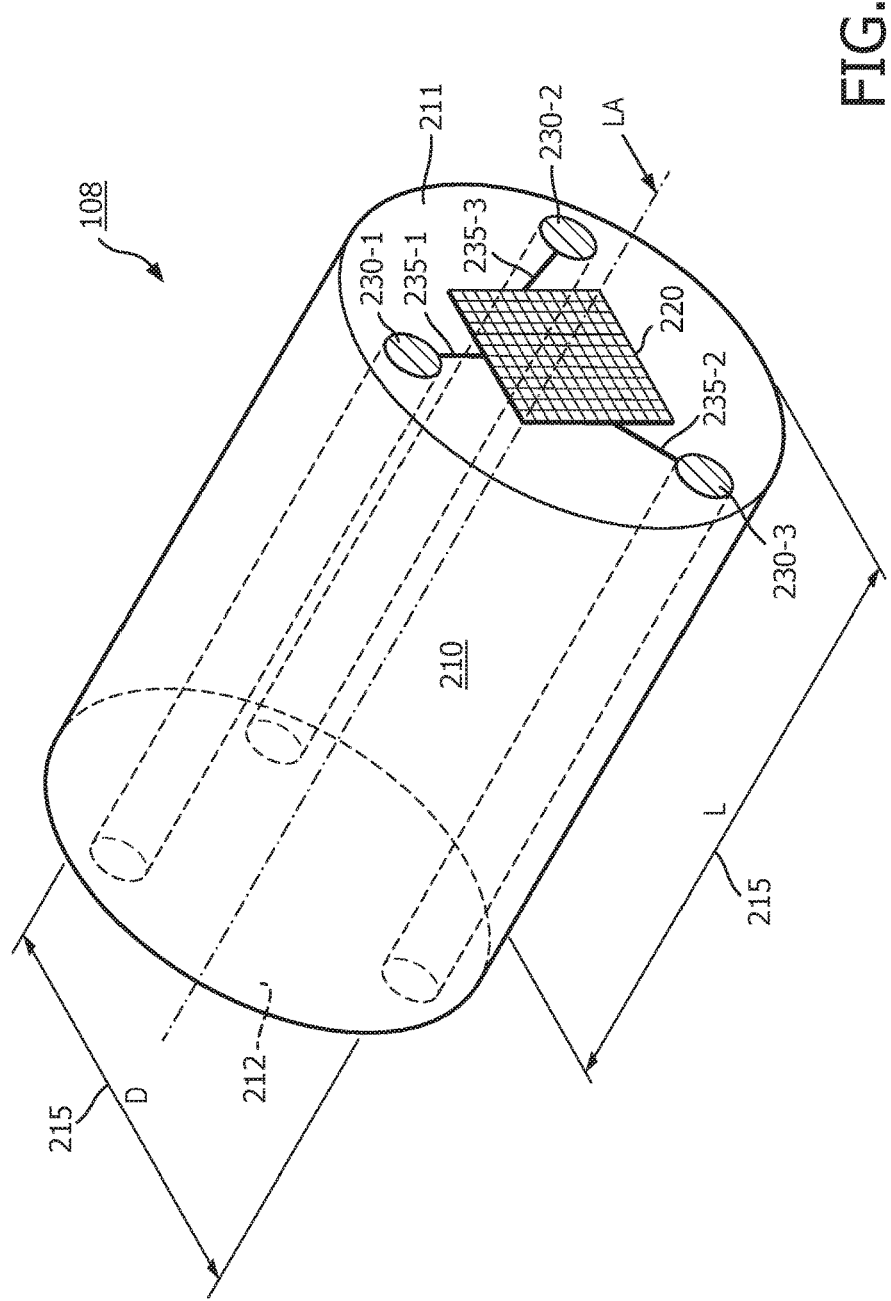
FIG. 2 is a diagrammatic perspective view of a sensor structure according to some embodiments.

FIG. 2 is a diagrammatic perspective view of sensor structure 108 for an end sensor 220 according to some embodiments. Sensor structure 108 includes a substrate 210 having a substantially cylindrical shape in the illustrated embodiment. Substrate 210 includes a distal surface 211 and a proximal surface 212, a diameter D 215 and a length L 216. Accordingly, L 216 may be as thin as 0.001 mm, or 1, 2, 3, 5 mm, or even longer, with some embodiments being about 0.1 mm, and other embodiments being about 0.5 mm. In some embodiments it is desirable to have a shorter L 216 to reduce impact on a bending stiffness. Embodiments using longer L 216 may include a robust protection to avoid bending. Bending is not desirable as it may break the coupling to the sensor or the sensor itself, with potential loss of signal. Accordingly, it is desirable to have an aspect ratio defined as length over diameter of less than approximately 2. For example, in an embodiment of a 0.014" (0.356 mm) diameter guide wire, where the component 108 may have a diameter of approximately 0.010" (0.25 mm), length L 216 may be as short as 0.020" (0.50 mm), or even less. Diameter D 215 may have a reduced dimension in order for sensor structure 108 to fit within intravascular device 100. In some implementations, the sensor structure 108 has a diameter D 215 that is sized to fit within a housing. For example, in some implementations the sensor structure is disposed within a housing having an opening through a sidewall to expose the sensor structure to ambient. In some particular embodiments, the housing containing the sensor structure is positioned between two flexible members (e.g., coils, polymer tubes, coil-embedded polymer tubes, and/or combinations thereof). The sensor structure 108 may be secured to the housing any suitable techniques, including adhesive. For example, in some instances the sensor structure 108 is mounted lengthwise within a housing similar to that described in U.S. Pat. No. 7,967,762 entitled "Ultra Miniature Pressure Sensor," the contents of which are herein incorporated by reference in their entirety, for all purposes. Accordingly, in some embodiments diameter D 215 may be 2 mm, 1 mm, 500 μm, or less. For example, for guide wires having an OD of about 0.0145" (0.37 mm), D 215 may be smaller than about 0.0115" (0.29 mm). For guide wires having an OD of about 0.018" (0.46 mm), D 215 may be as large as 0.0145" (0.37 mm). And for guide wires having an OD of about 0.035" (0.89 mm), D 215 may be as large as 0.030" (0.76 mm). This technology is particularly suitable for the severely space constrained geometries of smaller guide wires.

Substrate 210 may be made of silicon or any other material used in a semiconductor foundry, such as germanium, silica, quartz, glass, sapphire, or any ceramic material. Substrate 210 includes electrodes 230-1, 230-2, and 230-3 (collectively referred to hereinafter as electrodes 230). In some embodiments electrodes 230 include conductors formed of gold, silver, copper, aluminum, or any other conducting material. In some embodiments, the end sensor 220 includes a flexible membrane positioned over a cavity such that the flexible membrane seals the cavity. The applied pressure causes the membrane to deflect into the cavity in varying amounts. In some instances, the membrane is embedded with conductive materials that are patterned to form a piezoresistive, capacitive, nanowire, nanofiber, and/or other suitable pressure transducing circuit elements. Accordingly, the pressure applied to the membrane causes the membrane to flex, which causes the embedded circuit to change resistance, capacitance, and/or other measurable characteristic that can be correlated to the applied pressured. The membrane may have a square, rectangular, circular, elliptical, other geometrical, and/or non-geometrical shape.

End sensor 220 is coupled to electrodes 230 by conductors 235-1, 235-2, and 235-3 (collectively referred to hereinafter as conductors 235). Conductors 235 may be electrically conductive wires, conductive traces, or doped semiconductor materials. Electrodes 230 may be formed within vias etched through a silicon substrate (e.g., cylindrical substrate 210) using semiconductor manufacturing techniques. In other embodiments, the electrodes 230 are formed in recesses formed in an outer surface of the silicon substrate. Accordingly, electrodes 230 are disposed longitudinally, either through the substrate 210 or along a surface of the substrate 210, in a direction that is parallel to the LA.

In some instances, each electrode 230 has a proximal end adjacent to or at proximal surface 212 and an opposing distal end adjacent to or at distal surface 211. In other instances, the proximal end of each electrode is spaced distally from the proximal surface 212. In that regard, by keeping space within the through vias and/or the recesses in the outer surface of the substrate 210, conductors that are to be electrically coupled to the electrodes 230 can be at least partially positioned within the through vias and/or recesses where they are electrically coupled to the electrodes. For example, in some instances distal sections of the conductors are positioned within the through vias and/or recesses such that distal ends of the conductors are positioned adjacent to and/or in contact with proximal ends of the electrodes. Then solder, welding, and/or other suitable conductive coupling mechanism is utilized to secure and electrically couple the conductors to the electrodes.

End sensor 220 is disposed on distal surface 211, facing outwards, in the distal direction. Embodiments consistent with this configuration reduce the constraint for having a thin sensor layer in a cantilevered configuration. Further, the mechanical robustness of substrate 210 relieves sensor 220 from stress in the core wire and/or other portions of the guide wire. In addition, since distal surface 211 is aligned in a direction substantially parallel to a torque rotating core member 135 about the LA, sensor 220 is decoupled from stresses arising from torsional effects. Such configuration reduces design concerns about the fabrication process of sensor circuit 220, relaxing geometrical and mechanical constraints.

In some embodiments, sensor 220 includes circuits and structures such as a micro-electromechanical system (MEMS), formed on a wafer. In some embodiments, end sensor 220 may be formed using semiconductor manufacturing techniques such as etching, deposition, and implantation of conductive layers on a substrate. When sensor 220 faces the distal direction, sensor 220 may have a thickness that reduces limitations to the placement of intravascular device 100 within a blood vessel. Thus, the wafer used for making sensor 220 may be a thin wafer (approximately 50 to 100 µm), an ultra-thin wafer (less than 50 µm and as thin as 1 µm), or a wafer of regular thickness (typically 300 to 700 µm). For example, in some embodiments the entire component 108 including sensor 220 may be formed on a 400 to 600 µm thick wafer which also provides substrate 210, and include electrodes 230 formed in vias through the wafer. In this context, the generally cylindrical cross-sectional profile of the component 108 is produced by an etching process such as deep reactive ion etching. In the case where the cross-sectional profile intersects one or more of the through wafer vias, those vias become recesses in the surface of the substrate 210. Accordingly, sensor 220 may include a circuit and/or structure such as a MEMS manufactured using a Deep Reactive Ion Etching (DRIE) technique, as disclosed in detail in U.S. patent application Ser. No. 11/864,499, entitled "Intravascular Pressure Devices Incorporating Sensors Manufactured Using Deep Reactive Ion Etching," filed Sep. 28, 2007, the contents of which are incorporated herein by reference in their entirety, for all purposes.

Figure 3:
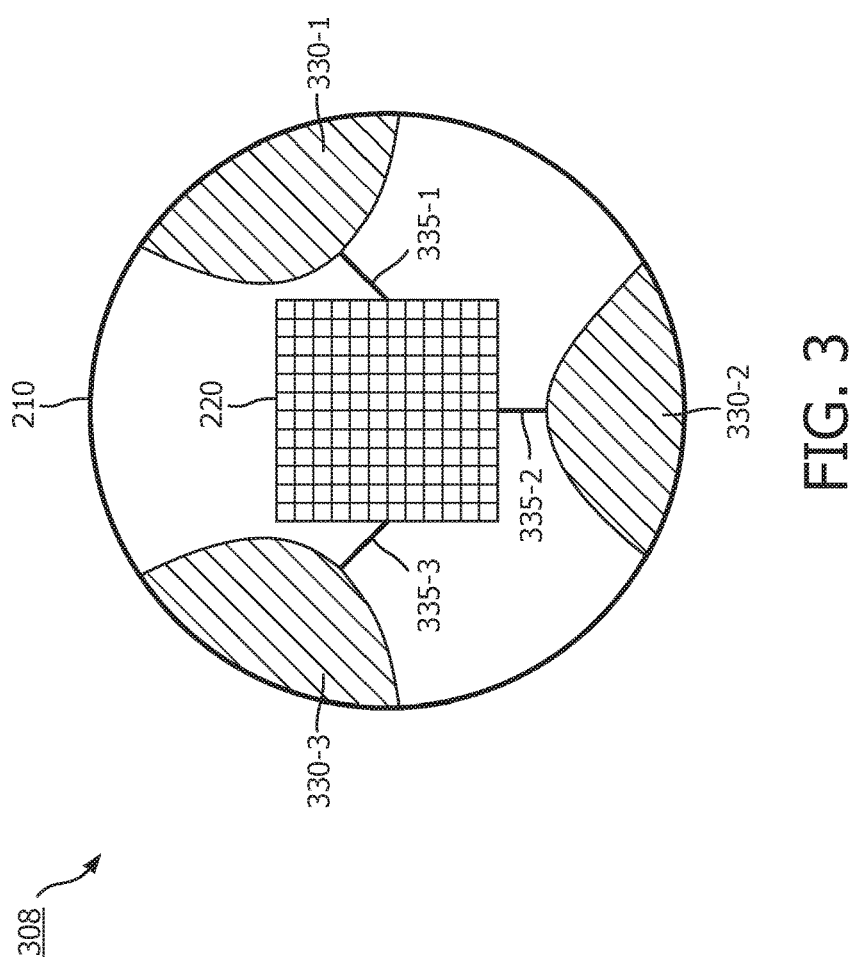
FIG. 3 is a diagrammatic partial cross-sectional front view of a sensor structure according to some embodiments.

FIG. 3 is a diagrammatic end view of a sensor structure 308 for end sensor 220 according to some embodiments. Accordingly, sensor structure 308 includes substrate 210 having a substantially cylindrical shape. Also, sensor structure 308 includes electrodes 330-1, 330-2, and 330-3 (collectively referred hereinafter as electrodes 330). Electrodes 330 are coupled to end sensor 220 through conductors 335-1, 335-2, and 335-3, respectively (hereinafter referred to as conductors 335). Conductors 335 may be as conductors 235 described in detail above (cf. FIG. 2). Accordingly, electrodes 330 may be formed as indentions on substrate 210 with a conductive material deposited to fill in the structure, forming an approximately cylindrical shape. Furthermore, electrodes 330 may extend from a distal surface of sensor structure 308 (the surface including sensor 220) to a proximal surface of sensor structure 308, opposite the distal surface. In some implementations, the sensor structure 308 is coated with an insulating material after formation of the electrodes 330 and/or electrically coupling of the electrodes 330 to conductors of a communication cable.

Figure 4:
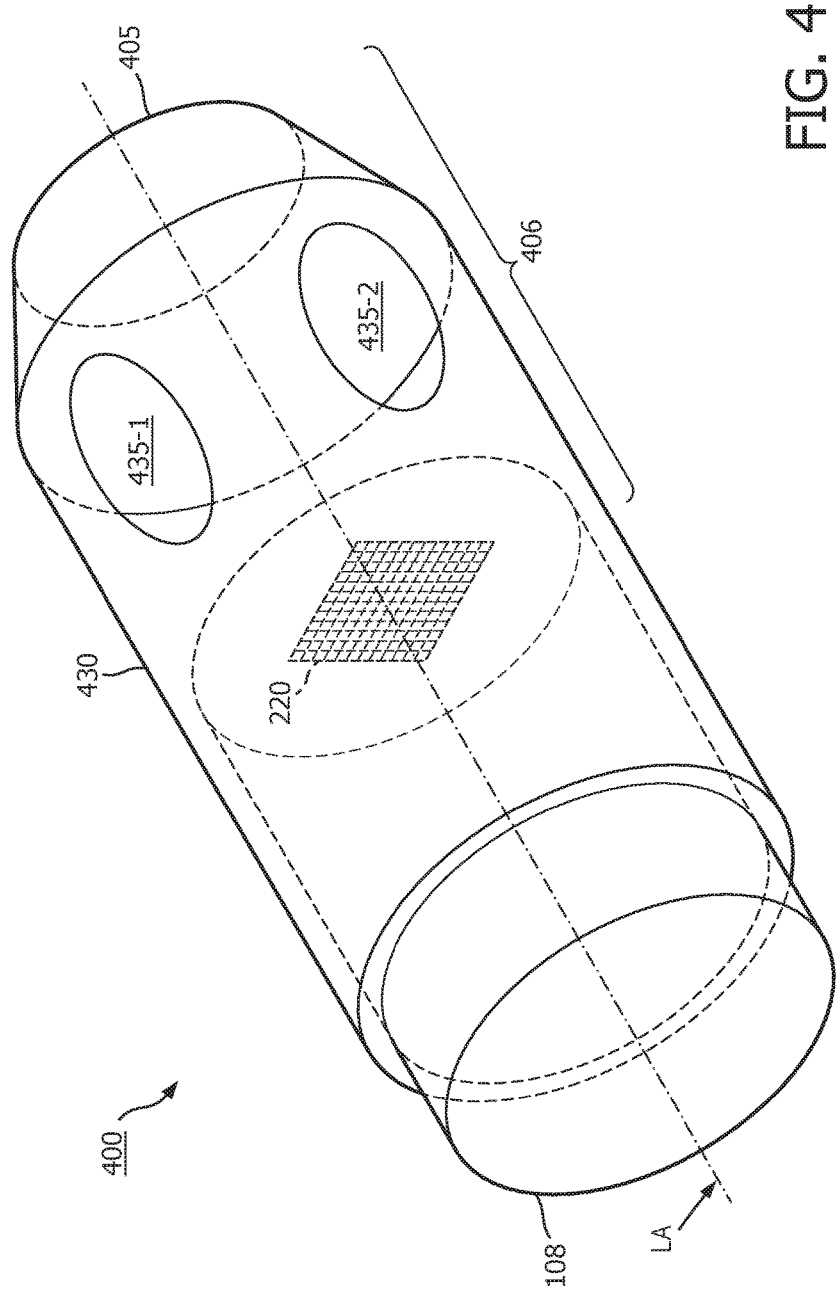
FIG. 4 shows a partial perspective view of a distal portion in an intravascular device according to some embodiments.

FIG. 4 shows a partial perspective view of a distal portion 406 of an intravascular device 400 according to some embodiments. Distal portion 406 of intravascular device 400 may include elements as distal portion 106 of intravascular device 100 described in detail above (cf. FIG. 1). For example, distal portion 406 includes sensor structure 108 having sensor 220 on a distal surface. In addition, distal portion 406 includes a portion of elongate flexible member 430 having holes 435-1 and 435-2 (collectively referred hereinafter as holes 435). Holes 435 expose sensor 220 to ambient fluid such as blood and other fluids present inside the blood vessel. Generally, the holes or openings 435 may have any shape, including geometrical (e.g., oval, circular, ellipse, rectangle, triangle, square, rhombus, etc.), non-geometrical, and/or combinations thereof. Likewise, the intravascular device 400 may include any number of openings to facilitate exposing the sensor 220 to the surrounding ambient fluid. In that regard, the number of openings may be dependent on the size and/or positioning of the openings.

FIG. 4 shows distal end 405 which may be as distal end 105 described in detail above (cf. FIG. 1). In addition, distal end 405 may have a tapered shape, as illustrated in FIG. 4. One of ordinary skill will recognize that the specific shape of distal end 405 is not limiting and a straight shape may be used for distal end 405. In some embodiments, the distal end 405 is closed. In other embodiments, the distal end 405 is open such that it provides a further passageway to expose the sensor 220 to the surrounding ambient fluid within the vessel.

Figure 5:
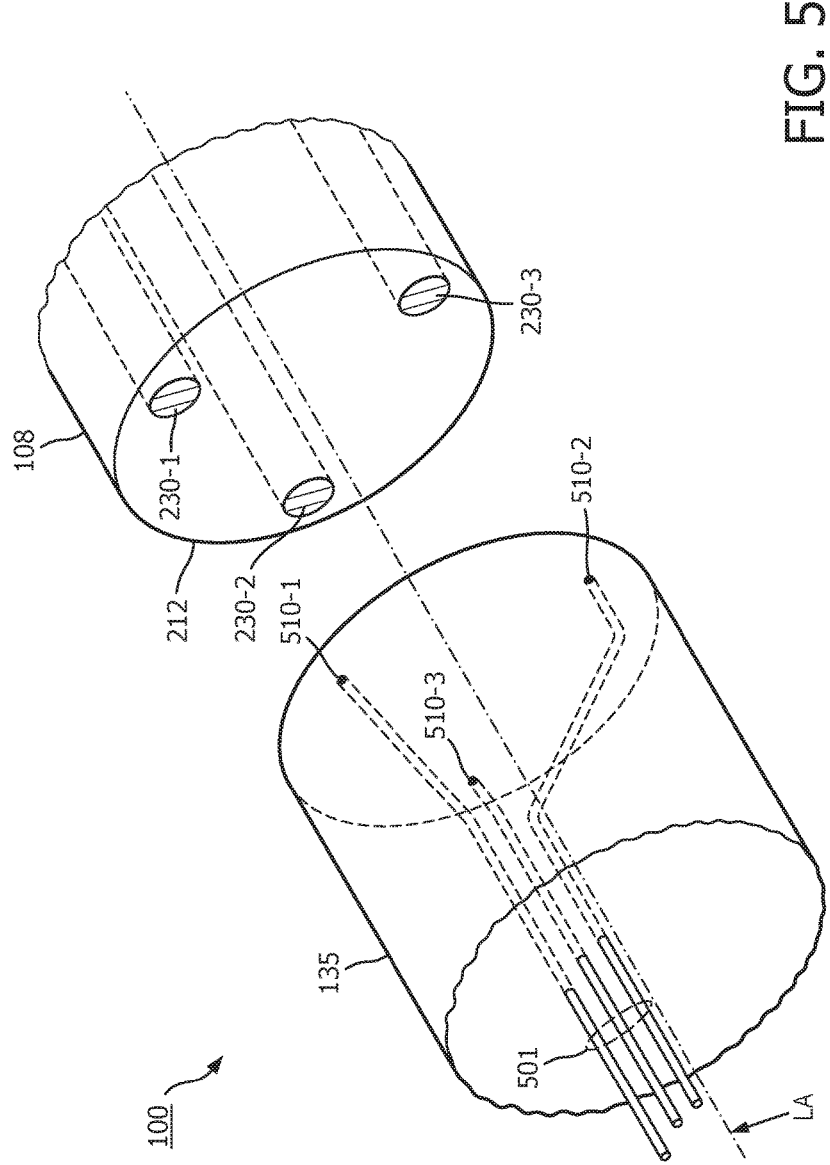
FIG. 5 shows a partial perspective view of a coupling for an end sensor in a sensor structure according to some embodiments.

FIG. 5 shows a partial perspective view of a coupling for an end sensor in sensor structure 108 according to some embodiments. Accordingly, the coupling in FIG. 5 forms an interface between core member 135 and sensor structure 108. FIG. 5 illustrates a cable 501 including three wires, or conductors. Cable 501 may be a trifilar cable as described in detail in U.S. provisional patent application No. 61/665,697, filed Jun. 28, 2012, and entitled "Intravascular Devices, Systems, and Methods," the contents of which are incorporated herein by reference in their entirety, for all purposes.

Cable 501 is separated into leads adjacent a distal surface of core member 135 facing a proximal surface 212 of sensor structure 108. In some embodiments, cable 501 includes electrical conductors or wires forming leads 510-1, 510-2, and 510-3 (collectively referred hereinafter as leads 510) that may be placed on a distal surface of core member 135. Thus, leads 510 end in a dot of solder material to make electrical contact with electrodes 230 in sensor structure 108 in some instances. In other instances, the leads 510 are at least partially positioned within the openings or recesses in which the electrodes 230 of the sensor structure 108 are formed. In some instances, a distal surface of the core member 135 and a proximal surface of the sensor structure 108 are abutted against each other. In some embodiments, sensor structure 108 may be glued to core member 135 using an adhesive or glue. In some embodiments, the adhesive may be urethane acrylate, cyanoacrylate, silicone, epoxy, and/or combinations thereof; the adhesive is selected to secure sensor structure 108 to core member 135. In some instances, the sensor structure 108 is flexibly connected to the core member 135. In yet other instances, the sensor structure 108 is not secured to the core member 135, but instead is held in place by attached conductive wires.

Embodiments consistent with the present disclosure provide a robust interconnect between cable 501 and electrodes 230. For example, as shown in FIG. 5 the electrical contact is sandwiched between a distal surface in core member 135 and proximal surface 212 in sensor structure 108. Furthermore, the interconnect configuration for sensor circuit 220 is fully within the flexible elongate member 102 of intravascular device 100, thus adding no extra constraints for device geometry. The conductors may take any suitable form, including without limitation flex-foil, spiral wrapped, direct-write, wound wires, and/or combinations thereof.

Figure 6:
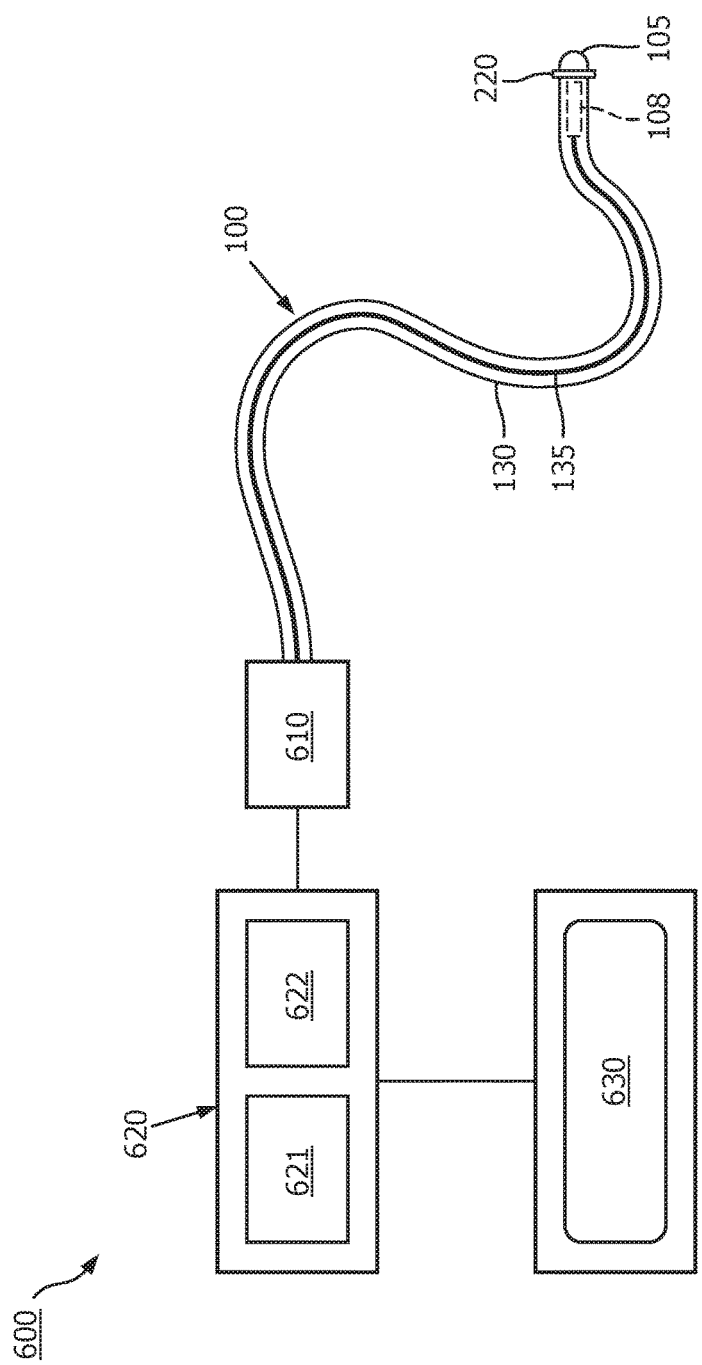
FIG. 6 shows a partial schematic view of a system for performing measurements using an end sensor exposed to an intravascular environment according to some embodiments.

FIG. 6 shows a partial schematic view of a system 600 for performing measurements using an end sensor exposed to an intravascular medium. System 600 includes an intravascular device 100; an interface device 610 coupled to the intravascular device; a control console 620 including a processor circuit 621; and a display unit 630. The intravascular device 100 may be similar to those described above, including having a sensor structure similar to those described above.

Interface device 610 may include electronic circuits configured to provide power and signals to sensor circuit 220. Electronic circuits in interface device 610 may also be configured to receive and process signals from sensor circuit 220. For example, interface device 610 may include an analog-to-digital converter, enabling interface device 610 to perform analog-to-digital conversion of signals provided by sensor circuit 220. Console 620 may control the operation of interface device 610 by providing power and receiving the sensor circuit data processed by interface device 610. Once the data is processed and further analyzed in console 620, an image may be displayed on display unit 630. For example, an image may include a graphic display and charts representing pressure values along a longitudinal direction in a blood vessel.

Figure 7:
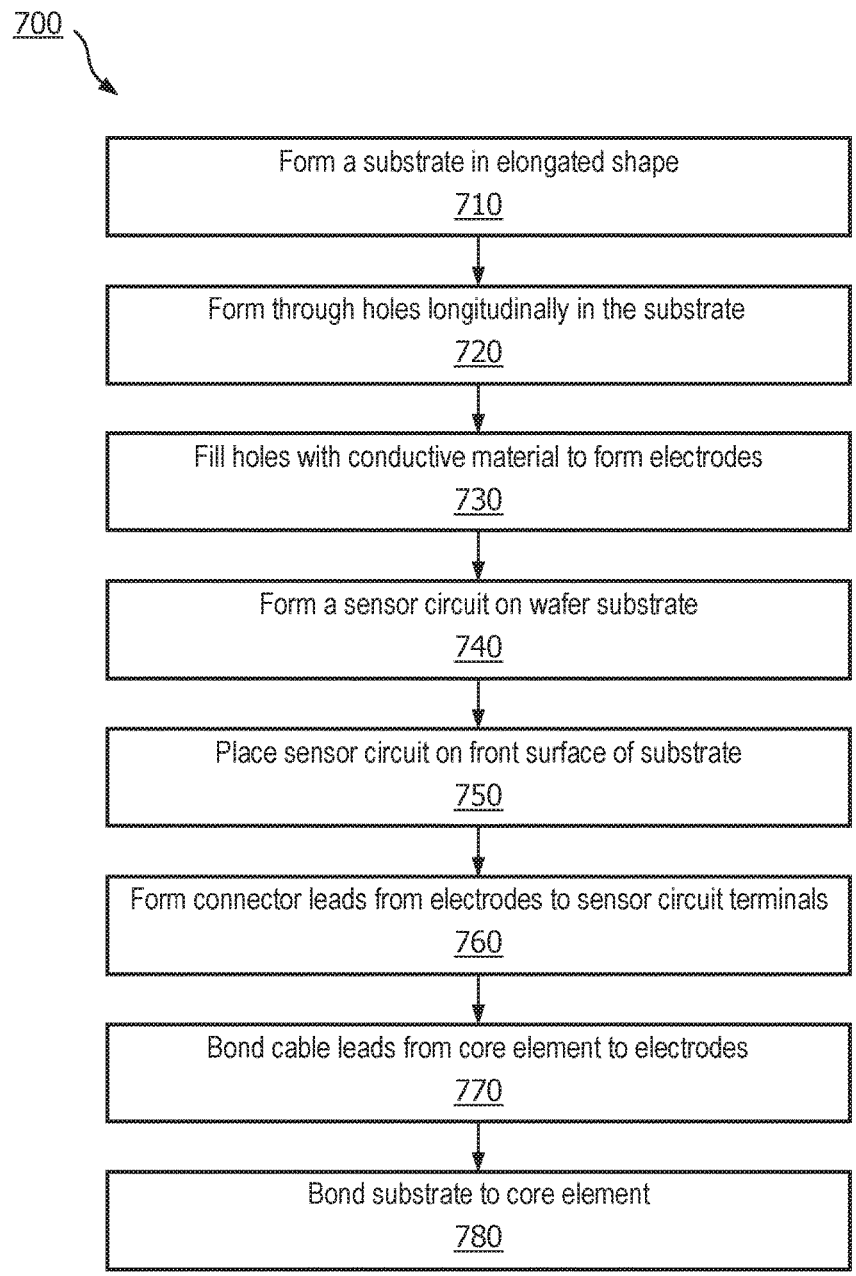
FIG. 7 shows a flow chart for a method of manufacturing an intravascular device having an end sensor, according to some embodiments.

FIG. 7 shows a flow chart for a method of manufacturing an intravascular device having an end sensor, according to some embodiments. Steps in method 700 may be performed manually by an operator, or automatically by a machine controlled by a computer having a processor circuit and a memory circuit. Further, according to some embodiments, steps in method 700 may be partially performed by an operator and some steps may be partially performed automatically by a machine controlled by a computer. The intravascular device in method 700 may be similar to one or more embodiments described in the present application. In some instances, the intravascular device includes a core element, a sensor structure for a sensor, and a flexible member. Furthermore, the intravascular device of method 700 may include a cable extending along the core member to provide power and collect data from the sensor (e.g., cable 501).

In some aspects, the end sensors of the present disclosure rely upon manufacturing techniques similar to those used for existing products, but with some important differences. One particular important difference is that the end sensor is not thinned in the manner of existing products. For example, in some implementations existing products remove back-side material of a wafer until the thickness of the resulting sensor device is ~0.050-0.075 mm. A thin sensor device is important in some existing products because the device is placed in a horizontal orientation (with the membrane facing parallel to the longitudinal axis) and must fit within the 0.356 mm diameter constraint of the guide wires in which they are utilized. By placing the sensor with the membrane facing perpendicular to the longitudinal axis—toward the distal (or proximal) end of the guide wire in accordance with the present disclosure, the length or thickness of the sensor can be optimized for strength, flexibility, connectivity, and/or combinations thereof.

In step 710 a substrate is formed in an elongated shape. Accordingly, the elongated shape is substantially cylindrical in some instances, with a longitudinal axis parallel to the LA of the intravascular device, and a front surface substantially perpendicular to the LA. However, the substrate may have other elongated shapes in other implementations, including elongated shapes having cross-sectional profiles that are geometrical, non-geometrical, and/or combinations thereof. The front surface is formed substantially planar with a circular cross-sectional profile in some instances. In some embodiments, step 710 includes forming an elongated substrate having a length of a few mm, such as 1, 2, 3, 5 mm, or even longer. In some embodiments it is desirable to have a shorter length to reduce impact on a bending stiffness. Embodiments using longer length may include a robust protection to avoid bending. Bending is not desirable as it may break the coupling to the sensor or the sensor itself, with potential loss of signal. Accordingly, it is desirable to have length as short as 0.020" (0.50 mm), or even less. Step 710 may include forming an elongated substrate having a cross-sectional profile (e.g., a cylindrical shape with a circular cross-sectional profile having a diameter) with a width or diameter of about 2 mm, 1 mm, 500 µm, or less. For example, for wires having an OD of about 0.0145" (0.37 mm), the diameter may be smaller than about 0.0115" (0.29 mm). For wires having an OD of about 0.018" (0.46 mm), the diameter may be as large as 0.0145" (0.37 mm). And for wires having an OD of about 0.035" (0.89 mm), the diameter may be as large as 0.030" (0.76 mm). In some embodiments step 710 may include forming a substrate from silicon, germanium, or an alloy of silicon and germanium, using semiconductor fabrication techniques. Materials used in step 710 may depend on the specific application and are not limiting of embodiments consistent with the present disclosure. In general, materials used in step 710 may be any material used in a semiconductor foundry, such as silica, quartz, glass, sapphire, any ceramic material, or even a plastic such as vinyl.

In step 720 through holes and/or recesses are formed in the substrate. In some embodiments, step 720 may include etching through holes parallel to the LA of the elongated substrate in step 710. Accordingly, step 720 may include forming holes as through silicon vias in an elongated silicon substrate provided in step 710. In some embodiments, step 720 may include forming longitudinal notches or indentations on a side surface of the elongated substrate in step 710. In some embodiments, step 720 may be performed using semiconductor fabrication techniques such as ion beam bombardment. In some embodiments, step 720 may include forming a micro-extrusion in the substrate and subsequently attaching the extruded portion to a functional cap.

In step 730 the through holes and/or recesses formed in step 720 are at least partially filled with a conductive material to form electrodes. Step 730 may include techniques such as flowing, sputtering, and/or vapor deposition of a conductive material inside the through holes and/or recesses formed in step 720. Step 730 may include using a conductive material such as gold, silver, copper, aluminum, an alloy of the above, or any combination of the above to at least partially fill the through holes and/or recesses.

In step 740 a sensor circuit is formed on a wafer substrate. For example, step 740 may include a DRIE process to form a MEMs circuit on a substrate. In some instances, an off-the-shelf pressure sensor is provided. In some instances, a pressure sensor diaphragm and resistor arrangement similar to that described in U.S. Pat. No. 7,967,762, entitled "Ultra Miniature Pressure Sensor," is utilized.

In step 750 the sensor circuit is placed on the front surface of the elongated substrate. Accordingly, step 750 may include using an adhesive to securely place the sensor circuit on the elongated substrate. In some embodiments, step 750 may include bonding the sensor circuit on the front surface of the elongated substrate using semiconductor manufacturing techniques, such as flip-chip techniques. The front surface of the elongated substrate in step 750 may be a surface substantially perpendicular to the LA of the elongated substrate.

In step 760 conductors are formed joining the electrodes to the sensor circuit terminals. In some embodiments, step 760 may include forming conductors using semiconductor manufacturing techniques for depositing conducting elements along a track. In some embodiments, step 760 may include depositing semiconductor materials and dopants along trenches in the front surface of the elongated substrate. The tracks or trenches used in step 760 may join the electrodes formed in the elongated substrate to the sensor circuit terminals. Step 760 may include performing procedures used in the semiconductor manufacturing industry such as photolithography and DRIE. Step 760 includes forming tracks and trenches on the elongated substrate and depositing materials on the tracks and in the trenches. Ion beam deposition, sputtering, vapor deposition, and annealing are procedures that may be included in step 760, according to some embodiments.

In step 770 cable leads are electrically coupled to the electrodes formed in step 730. Step 770 may include forming bonds on a back surface of the elongated substrate including the electrodes. The back surface may be substantially perpendicular to the LA of the elongated substrate, and opposite to the front surface having the sensor circuit according to step 750. Cable leads in step 770 may include three wires, each connected to a separate node of the circuit. For example one wire may be connected to the ground node of the measurement circuit, while the other two wires may be connected to signal nodes which carry electrical signals representing the measurement of interest, such as pressure.

In step 780 the elongated substrate is bonded to the core member or other structure of the intravascular device. Accordingly, step 780 may include bonding a distal surface in the core member to a proximal surface in the elongated substrate using an adhesive. The proximal surface in the elongated substrate may be the back substrate having bonds to the electrodes as in step 770. In some instances, the elongated substrate is bonded to a component or components of the intravascular device other than the core member, such as a housing, a flexible element (e.g., coil, polymer tubing, coil-embedded polymer tubing, etc.), or otherwise.

Figure 8:
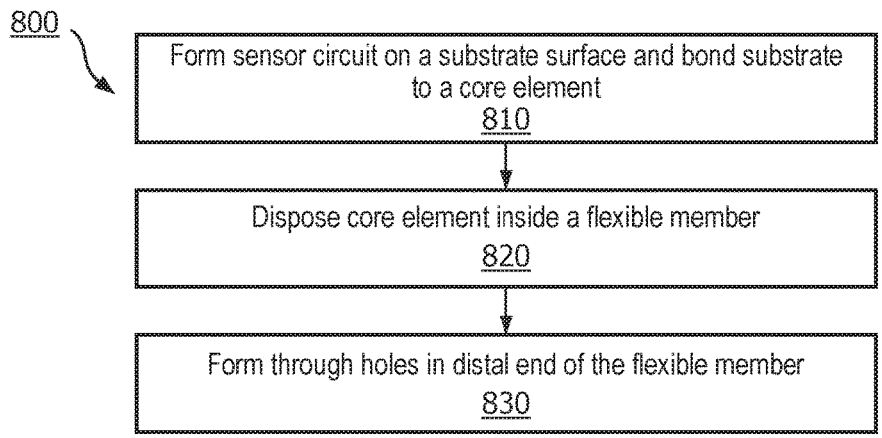
FIG. 8 shows a flow chart for a method of manufacturing an intravascular device having an end sensor, according to some embodiments.

FIG. 8 shows a flow chart for a method of manufacturing an intravascular device having an end sensor, according to some embodiments. Steps in method 800 may be performed manually by an operator, or automatically by a machine controlled by a computer having a processor circuit and a memory circuit. Further according to some embodiments some steps in method 800 may be partially performed by an operator and some steps may be partially performed automatically by a machine controlled by a computer. The intravascular device in method 800 may include features similar to the intravascular devices described above.

In step 810 a sensor circuit is formed on a substrate surface. Also in step 810, the substrate is bonded to a core member, housing, flexible element (e.g., coil, polymer tubing, coil-embedded polymer tubing, etc.), and/or other element to form an intravascular device, such as a guide wire. Accordingly, in some embodiments step 810 may include performing one or more of steps 710 through 780 in method 700, as described in detail above.

In step 820 the core member is disposed inside a flexible member of the intravascular device. In step 830 one or more through holes or openings are formed in a distal portion of the flexible member of step 820. For example, the through holes may be through a side wall of the flexible member, through a side wall of a housing, and/or other portion of the flexible member to expose the sensor circuit of step 810 to ambient (e.g., through holes 435, cf. FIG. 4).

Figure 9:
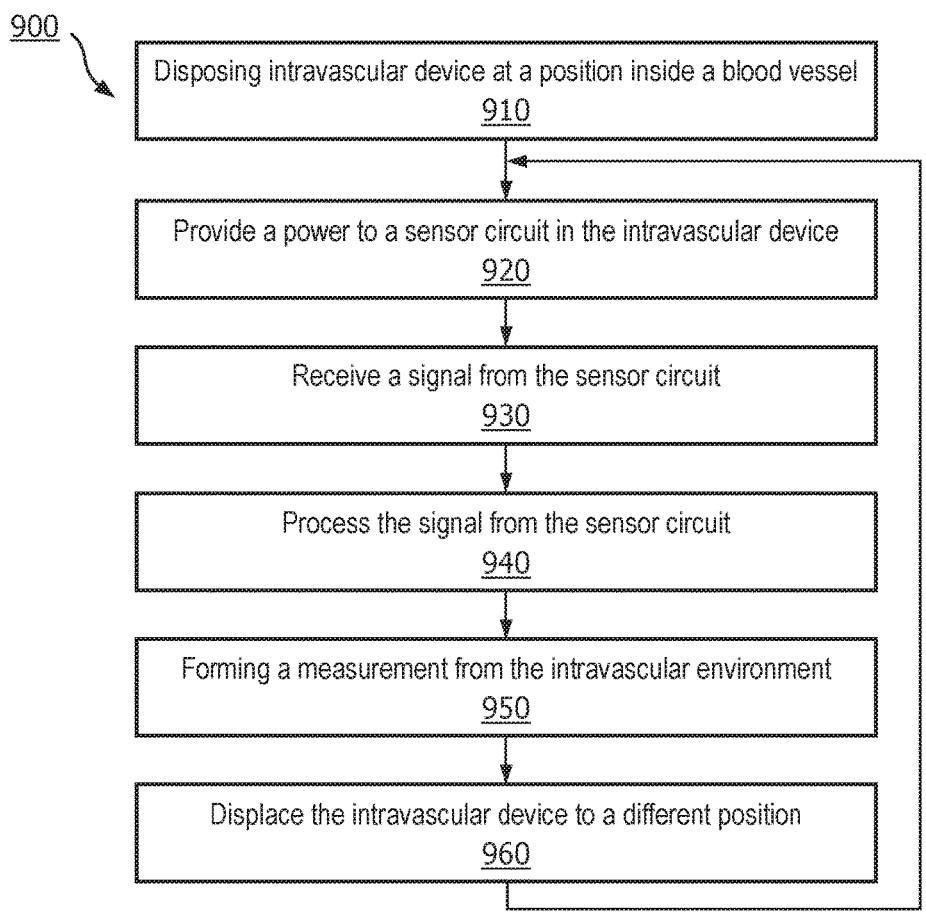
FIG. 9 shows a flow chart for a method of obtaining a measurement of an intravascular environment, according to some embodiments.

FIG. 9 shows a flow chart for a method 900 of obtaining a measurement of an intravascular environment, according to some embodiments. Method 900 may be partially performed by an operator using a system for performing measurements with an end sensor exposed to an intravascular environment, such as system 600 described in detail above (cf. FIG. 6).

In step 910 the intravascular device is disposed at a position inside a blood vessel. In step 920 a power is provided to a sensor circuit in the intravascular device, wherein the sensor circuit is disposed substantially perpendicular to a longitudinal axis of the intravascular device (e.g., sensor circuit 220, cf. FIG. 2). In some embodiments, step 920 may include providing a voltage to a cable running along the intravascular device (e.g. cable 501, cf. FIG. 5). Further according to some embodiments, step 920 may include providing an optical signal to an optical fiber in a cable running along the intravascular device. To that end, in some instances the pressure sensor is an optical pressure sensor as disclosed in one or more of U.S. Pat. No. 7,689,071, entitled "FIBER OPTIC PRESSURE SENSOR FOR CATHETER USE," U.S. Pat. No. 8,151,648, entitled "ULTRA-MINIATURE FIBER-OPTIC PRESSURE SENSOR SYSTEM AND METHOD OF FABRICATION," U.S. application Ser. No. 13/415, 514, entitled "MINIATURE HIGH SENSITIVITY PRESSURE SENSOR," each of which is incorporated by reference in its entirety, for all purposes. Accordingly, step 920 may be performed by the control console through the interface device.

In step 930 a signal from the sensor circuit is received. For example, the signal may be received in the interface device. In step 940 the signal from the sensor circuit is processed. For example, in some embodiments an analog signal may be converted to a digital signal in the interface device. In step 950 a measurement from the intravascular environment is formed. Accordingly, step 950 may be partially performed using the processor circuit and the memory circuit in the control console. In some embodiments, step 950 may include storing the processed signal from the sensor circuit and/or storing the position of the intravascular device inside the blood vessel. For example, the processed signal and the associated position of the intravascular device may be stored in the memory circuit in the control console in some instances. In some embodiments, step 950 may include displaying the measurement in the display unit. In step 960 the intravascular device is displaced to a different position and another measurement is obtained by repeating one or more of steps 920, 930, 940, and 950.

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:

1. An intravascular sensor assembly comprising:
a flexible elongate member having a longitudinal axis (LA);

a core member disposed inside the flexible elongate member;

an electrical conductor extending along the core member; and an elongated, cylindrical-shaped substrate disposed distal to the core member and inside the flexible elongate member, the elongated, cylindrical-shaped substrate comprising:

a proximal surface and an opposing distal surface;

a semiconductor material;

at least one electrode disposed within at least one recess in an outer surface of the elongated, cylindrical-shaped substrate, the at least one recess extending in a longitudinal direction, wherein the at least one electrode comprises a proximal end surface substantially coplanar with the proximal surface of the elongated, cylindrical-shaped substrate and a distal end surface substantially coplanar with the distal surface of the elongated, cylindrical-shaped substrate, wherein the electrical conductor is coupled to the at least one electrode at the proximal end surface; and a sensor circuit disposed on a distal surface of the elongated, cylindrical-shaped substrate, the sensor circuit coupled to the distal end surface of the at least one electrode, wherein the sensor circuit comprises an intravascular pressure sensor circuit.

2. The intravascular sensor assembly of claim 1 wherein the sensor circuit is a pressure sensor circuit.

3. The intravascular sensor assembly of claim 1 wherein the at least one electrode comprises three electrodes configured to be coupled to three different terminals of the sensor circuit.

4. The intravascular sensor assembly of claim 1 wherein the flexible elongate member comprises at least one through hole at a distal end so as to expose the sensor circuit to an intravascular ambient.

5. The intravascular sensor assembly of claim 1 wherein the elongated, cylindrical-shaped substrate includes a cylindrical axis along the LA.

6. The intravascular sensor assembly of claim 1 wherein the elongated, cylindrical-shaped substrate is made of the semiconductor material selected from the group consisting of silicon, germanium, a silicon-germanium alloy, silica, quartz, sapphire, a ceramic material, a plastic material, and a combination thereof.

7. The intravascular sensor assembly of claim 1 further comprising a cable extending along the core member between a proximal portion and a distal portion of the flexible elongate member, the cable including the electrical conductor.

8. The intravascular sensor assembly of claim 1 wherein the sensor circuit comprises a micro-electromechanical system (MEMS).

9. The intravascular sensor assembly of claim 1 wherein the elongated, cylindrical-shaped substrate is bonded to the core member using an adhesive selected from the group consisting of urethane acrylate, cyanoacrylate, silicone, epoxy, and any combination thereof.

10. A sensor structure for use in an intravascular device assembly, the sensor structure comprising:

a substrate having an elongated cylindrical shape with a length defined along a longitudinal axis (LA) and a width extending perpendicular to the longitudinal axis, wherein the substrate includes a semiconductor material, the shape further comprising:

a proximal surface and an opposing distal surface, each extending substantially perpendicular to the LA; and an outer surface extending substantially parallel to the LA between the proximal and distal surfaces;

at least one electrode disposed longitudinally within at least one recess in the outer surface of the substrate, wherein the at least one electrode comprises an distal end surface substantially coplanar with the distal surface of the substrate and a proximal end surface substantially coplanar with the proximal surface of the substrate, and a sensor circuit disposed on the distal surface, the sensor circuit having at least one lead coupled to the distal end surface of the at least one electrode.

11. The sensor structure of claim 10 wherein the substrate is made of a material selected from the group consisting of silicon, germanium, a silicon-germanium alloy, quartz, glass, sapphire, a ceramic material, a plastic material, or a combination thereof.

12. The sensor structure of claim 10 wherein the sensor circuit is bonded to the distal surface in a flip chip configuration.

13. A system for performing measurements using a sensor exposed to an intravascular environment, the system comprising:

an intravascular device having:

a flexible elongate member having a longitudinal axis (LA);

a core member disposed inside the flexible elongate member;

an electrical conductor extending along the core member; and an elongated, cylindrical-shaped substrate disposed distal to the core member and inside the flexible elongate member, the elongated, cylindrical-shaped substrate comprising:

a proximal surface and an opposing distal surface;

a semiconductor material;

at least one electrode disposed within at least one recess in an outer surface of the elongated, cylindrical-shaped substrate, the at least one recess extending in a longitudinal direction, wherein the at least one electrode comprises a proximal end surface substantially coplanar with the proximal surface of the elongated, cylindrical-shaped substrate, wherein the electrical conductor is coupled to the proximal end surface of the at least one electrode; and a sensor circuit disposed on a distal surface of the elongated, cylindrical-shaped substrate, the sensor circuit coupled to the at least one electrode, wherein the sensor circuit comprises an intravascular pressure sensor circuit; and a control console coupled to the intravascular device.

14. The system of claim 13 further comprising an interface device positioned between the control console and the intravascular device, wherein the interface device provides power to the sensor circuit and processes a signal from the sensor circuit.

15. The system of claim 14 wherein the interface device comprises an analog to digital converting circuit to provide a digital signal to the console.

16. The system of claim 13 wherein the sensor circuit is a pressure sensor and the control console outputs a graph of a blood pressure along a longitudinal axis in the intravascular environment.

17. The system of claim 13 wherein the elongated, cylindrical-shaped substrate includes a cylindrical axis along the LA.

18. The system of claim 17 wherein the elongated, cylindrical-shaped substrate is bonded to the core member using an adhesive.

19. The intravascular sensor assembly of claim 1 wherein the distal surface extends perpendicular to the LA.

20. The sensor structure of claim 10 wherein the sensor circuit is formed on the distal surface of the substrate.

21. The system of claim 13 wherein the distal surface extends perpendicular to the LA.

22. The intravascular sensor assembly of claim 1, wherein the elongated, cylindrical-shaped substrate is coated with an insulating material.

23. The intravascular sensor assembly of claim 1, wherein the sensor circuit comprises at least one lead and the sensor circuit is coupled to the distal end surface of the at least one electrode through the at least one lead.

* * * * *